United States Patent [19]

Moll, III et al.

[11] Patent Number: 6,121,056

[45] Date of Patent: *Sep. 19, 2000

[54] RANDOM DETECTION OF ANTIGENS WITH ANTIBODIES IMMOBILIZED ON SOLUBLE SUBMICRON PARTICLES

[75] Inventors: Fred Moll, III, Pembroke Pines, Fla.; Charles Ferzli, Carrboro, N.C.; Spencer H. Lin, Coral Springs; Pratap Singh, Miami, both of Fla.

[73] Assignee: Dade Behring Inc., Deerfield, Ill.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/226,172

[22] Filed: Apr. 12, 1994

Related U.S. Application Data

[63] Continuation-in-part of application No. 08/021,928, Feb. 24, 1993, abandoned.

[51] Int. Cl.$^7$ .................................................. G01N 33/552
[52] U.S. Cl. ...................... 436/527; 435/7.93; 435/7.94; 436/500; 436/512; 436/530; 436/823; 530/391.1
[58] Field of Search ..................... 436/500, 512, 436/527, 530, 823; 435/7.93, 7.94; 530/391.1

[56] References Cited

U.S. PATENT DOCUMENTS

| | | | |
|---|---|---|---|
| 4,363,634 | 12/1982 | Schall, Jr. ................. | 436/531 |
| 4,444,879 | 4/1984 | Foster et al. .................. | 435/7 |
| 4,507,466 | 3/1985 | Tomalia et al. ........... | 528/332 |
| 4,517,288 | 5/1985 | Giegel et al. ............. | 435/188 |
| 4,568,737 | 2/1986 | Tomalia et al. ........... | 528/332 |
| 4,694,064 | 9/1987 | Tomalia et al. ........... | 528/332 |
| 5,204,448 | 4/1993 | Subramanian ............ | 530/408 |
| 5,242,804 | 9/1993 | Bahar et al. ............ | 435/7.93 |
| 5,338,532 | 8/1994 | Tomalia et al. .......... | 424/1.49 |
| 5,468,606 | 11/1995 | Bogart et al. ............... | 435/6 |
| 5,482,830 | 1/1996 | Bogart et al. ............ | 436/525 |

FOREIGN PATENT DOCUMENTS

| | | |
|---|---|---|
| 0481526 | 4/1992 | European Pat. Off. . |
| WO8801178 | 2/1988 | WIPO . |
| 9012050 | 10/1990 | WIPO . |
| 9306868 | 4/1993 | WIPO . |
| WO 94/03774 | 2/1994 | WIPO . |
| WO 91/12886 | 9/1994 | WIPO . |

OTHER PUBLICATIONS

Giegel et al., Clin. Chem. 28: 1894–98 (1982).
Roberts, J.C. et al., Using Starburst Dendrimers as Linker Molecules to Radiolabel Antibodies, Bioconjug. Chemistry 1: 305–308 (1990).
Singh et al. Amer. Chem. Soc. Symposium Series, vol. 70: Proceedings of the Amer. Chem. Soc. Div. of Polymeric Materials, Science and Engineering, San Diego, CA, pp. 237–238 (1994).

*Primary Examiner*—Mary E. Ceperley
*Attorney, Agent, or Firm*—Fish and Richardson

[57] ABSTRACT

Methods, compositions and articles of manufacture are provided for conducting specific binding assays to determine the concentration or presence of at least one analyte in a sample. At least two dendrimer-reagent preparations with different analyte specificities may be immobilized on a solid phase. Alternatively, at least one dendrimer-reagent preparation having multiple specificities may be immobilized on a solid phase. Immobilization is facilitated by coupling specific binding assay reagents such as polypeptide receptors or analytes with water soluble polymers. Such water soluble polymers, for example star polymers such as dendrimers, provide production advantages of lot-to-lot uniformity and homogeneity, and can enhance sensitivity due to low non-specific binding to the solid phase.

43 Claims, No Drawings

RANDOM DETECTION OF ANTIGENS WITH ANTIBODIES IMMOBILIZED ON SOLUBLE SUBMICRON PARTICLES

This is a continuation-in-part of application Ser. No. 08/021,928, filed Feb. 24, 1993, now abandoned.

FIELD OF THE INVENTION

This invention relates generally to methods for immobilizing specific binding assay reagents on a solid support. In particular this invention relates to a method for immobilizing multiple reagents on a solid phase support using water soluble polymers. This invention also relates to a solid phase support having immobilized multiple reagents useful in diagnostics tests.

BACKGROUND OF THE INVENTION

In vitro diagnostic assays may be used to measure amounts of an analyte found in a body fluid sample or tissue sample. The analyte must be distinguished from other components found in the sample. Analytes may be distinguished from other sample components by reacting the analyte with a specific receptor for that analyte. Assays that utilize specific receptors to distinguish and quantify analytes are often called specific binding assays.

The most common receptors are antibodies and specific binding proteins such as Intrinsic Factor or Folate Binding Protein. Receptors are characterized by having a reversible specific binding affinity for an analyte or an analogue of that analyte. As used herein, an analogue generally is an analyte derivative carrying a detectable marker such as an enzyme, fluorescent molecule or other known label. The analogue is capable of binding to a receptor with about the same specificity and affinity as the analyte.

In heterogeneous specific binding assays described in the technical and patent literature, the receptor or other assay reagent of the specific binding reaction is often immobilized on a solid phase. Immobilization of these reagents is required to separate the bound components (for example analyte bound to the solid phase through a receptor) from the unbound components.

The various methods by which a receptor or other reagent can be immobilized on a solid phase include adsorption, absorption or covalent bonding. However, many of the solid phase supports used in such assays are not inert, and may sequester proteins and other substances from the sample by non-specific binding. Although glass is a relatively inert substrate, generally it has been found to be unsatisfactory for use in solid phase binding assays. See, for example U.S. Pat. No. 3,790,653 for a discussion of inadequacies of glass substrates.

Recently, however, procedures have been described for immobilizing an essentially soluble immunocomplex of a reagent and an antiserum to the reagent on an inert glass fiber solid phase support. These procedures are disclosed in U.S. Pat. No. 4,517,288, incorporated by reference herein.

In these immunological immobilization procedures, soluble immunocomplexes are prepared by combining at least two immunochemically reactive substances with one another in solution. At least one of such immunochemically reactive materials is selected for its immunochemical specificity for an analyte of interest. For example, if the soluble immunocomplex is to be used in an immunoassay for the detection of thyroid stimulating hormone (TSH), then one component of the immunocomplex is selected for its immunochemical specificity for TSH. A typical example would be an antibody with specificity for TSH, i.e., an anti-TSH antibody. The second component of the immunocomplex could comprise an antibody preparation directed against the anti-TSH antibody. Antiserum to anti-analyte antibodies, for example to mouse anti-TSH antibodies, can be prepared by injecting purified mouse immunoglobulin G (IgG) into a host animal (i.e., goat), and thereafter harvesting the antiserum to the mouse IgG. The mouse anti-TSH antibody and the goat antiserum to mouse IgG are thereafter worked up as standard stock solutions.

Having prepared these stock solutions, a portion of each is combined in a buffered medium. The resulting immunocomplex, in an appropriate volume of buffer, is thereafter spotted onto a delimited area of a glass fiber filter. Alternatively, the two components of the immunocomplex may be applied to the filter as separate buffered solutions and allowed to react in situ. In both instances, the point of application of the immunocomplex defines a reaction zone within the solid phase. The applied immunocomplexes become adsorbed and entrapped within the interstices of the beds of fibers within the glass fiber filter. The method of application can include dispensing of the immunocomplex solution with a manual or automated pipette, or with other automated equipment including assay analyzer instruments. Subsequent to application of the immunocomplex to the solid phase and the elapse of a suitable incubation period, the solid phase is dried under controlled conditions thereby yielding a stable reactive reagent which can be used in any one of a number of solid phase specific binding assay protocols.

Immunological immobilization, although useful in a variety of assay formats, has been noted to include a number of inherent disadvantages. The presence of the additional immunoglobulins on the filter (e.g., antiserum to anti-analyte antibodies) can lead to nonspecific binding of proteinaceous and other biological materials. This can significantly decrease assay sensitivity. Moreover, given the inherent variability of IgG preparations from separate immunizations of the same or different host animals, lot-to-lot variability in titer, purity, specificity and affinity of IgG preparations must be accounted for in manufacturing procedures. Similarly, variability in production of solid phase reagents may be encountered due to the tendency of immunocomplexes to become inhomogeneously distributed within stock solutions. That is, such immunocomplexes, while substantially soluble, may not remain completely soluble and may undergo some settling out of solution over time. Even with periodic mixing of stock solutions, gravitational influences, temperature gradients and other physical influences can cause subtle inhomogeneities within solutions applied to the solid phase reagents.

Starburst™ dendrimers (manufactured by The Dow Chemical Company) are polymers of spherical or other three-dimensional shapes that have precisely defined compositions and that possess a precisely defined molecular weight. Such dendrimers can be synthesized as water soluble macromolecules through appropriate selection of internal and external moieties. See U.S. Pat. Nos. 4,507,466 and 4,568,737, incorporated by reference herein. Dendrimers may be conjugated with various pharmaceutical materials as well as with various targeting molecules that may function to direct the conjugates to selected body locations for diagnostic or therapeutic applications. See for example, WO 8801178, incorporated by reference herein. Starburst dendrimers have been used to covalently couple synthetic porphyrins (e.g., hemes, chlorophyll) to antibody molecules as a means for increasing the specific activity of radiolabeled antibodies for tumor therapy and diagnosis. Roberts, J. C. et al., Using Starburst Dendrimers as Linker Molecules to Radiolabel Antibodies, *Bioconjug. Chemistry* 1:305–308 (1990).

Applicants have discovered that dendrimers can be used in place of antiserum to facilitate immobilization of assay reagents on the solid phase. That is, dendrimers can be covalently coupled to assay reagents such as antibodies or even relatively small molecules, and then immobilized on glass fiber filters. In comparison to immunological immobilization, immobilization utilizing dendrimer complexes presents a number of distinct advantages. First, the dendrimers are produced with precise polymer chemistries and can be designed to have a precise number of generations yielding a precise molecular size, weight and surface composition. Because of the uniform and characterized chemistries, such parameters remain uniform over different manufacturing lots. Second, the dendrimers, depending on interior and surface compositions, can be manufactured to be water soluble such that the dendrimer-reagent conjugates remain in solution and maintain solution homogeneity over time. This eliminates lot-to-lot nonuniformity due to inhomogeneous distribution of immunological conjugates in solution. Third, the chemistries for attachment of reagents to the dendrimers are well characterized and are not subject to the variations inherent in associations of antisera and antibody binding substances. Antisera are subject to variations in affinity, specificity, and immunoglobulin purity, none of which are encountered during production of dendrimer-reagent conjugates.

For these reasons, dendrimer-based solid phase reagents are readily prepared having substantial lot-to-lot uniformity. Moreover, since stock or commercial solutions of dendrimer conjugates retain homogeneity over substantial periods of time, it is possible for end users of commercial assay instruments to prepare these solid phase reagents on site. The use of freshly prepared solid phase reagents further eliminates additional variables that may enter into distribution and commercial use of pre-prepared solid phase reagents, such as changes due to long term storage, temperature of storage, and other storage variables.

Some specific binding assays have been automated. A majority of the currently available automated assay systems, however, allow the detection of only one analyte in each cycle. Thus, in order to analyze more than one analyte in a single sample, one must wait for the testing cycle of a first analyte to be completed before a second analyte in the same sample can be tested and quantified. For most automated instruments a cycle time is usually at least 40 minutes. Alternatively, the sample to be analyzed could be aliquoted into multiple testing samples and analyzed simultaneously to obtain the desired quantification information. This second approach not only requires a greater amount of the patient sample, but also necessitates additional capital expenditure in order to operate multiple analyzers simultaneously.

A limited number of random access enzyme immunoassay (EIA) systems utilize a unit dose concept in order to analyze more than one analyte in a given sample. In these systems, all the required reagents such as the immobilized antibody, antibody-enzyme or drug-enzyme conjugate and the substrate required for the generation of the signal, are packaged together in a single packet and each packet contains reagents sufficient for a single analysis. This single packet system is more expensive than bulk storage and packaging. The added expense reflects, for example, the cost of separately packaging each component required for an assay, specific requirements of the packaging material allowing maximum stability of the reagents, and the extra storage space needed for each unit dose. In addition, the time required for incubations at different steps of the assay causes the over-all time for generation of results to be longer for these random access assay systems.

SUMMARY OF THE INVENTION

The present invention includes methods of conducting specific binding assays to determine the concentration or presence of at least one analyte in a sample. At least two dendrimer-reagent preparations are made where each preparation comprises a plurality of dendrimer-reagent complexes having a defined analyte specificity. The analyte specificities differ for each preparation. Effective amounts of the preparations are applied to a delimited area of a solid phase under conditions effecting immobilization of the dendrimer-reagent complexes on the solid phase. The dendrimer-reagent preparations can be mixed together to form a mixture solution prior to being added to the solid phase. A sample is applied under binding conditions to the solid phase. A selected amount of an indicator or a labeled specific competitive reagent is added to the solid phase. The amount of indicator or label bound to the solid phase is determined and correlated to the concentration or presence of at least one analyte in the sample.

The complexes used in the method comprise dendrimers coupled to reagents. The reagents can be, without limitation, antibodies or antibody fragments, specific binding proteins, or analytes. The sample and indicator can be applied simultaneously or sequentially to the solid phase.

The present invention further includes a method for immobilizing at least two specific binding assay reagents with different analyte specificities on a solid phase. The reagents can be, without limitation, antibodies, antibody fragments, specific binding proteins or analytes. The reagents are coupled to dendrimers by coupling methods that include but are not limited to the formation of carbon-sulfur (C-S) linkages.

The present invention also includes a solid phase composition for use in a specific binding assay. The solid phase composition includes a solid phase comprising a mat of compressed fibers, and an analyte-binding component comprising at least two dendrimer-reagent preparations. Each preparation comprises a plurality of dendrimer-reagent complexes having a defined analyte specificity. The analyte specificities differ for each preparation. The reagents can be, without limitation, antibodies, antibody fragments, specific binding proteins or analytes. The preparations are immobilized on a delimited area of the solid phase. The solid phase can be a glass fiber filter.

The present invention further relates to methods of conducting specific binding assays to determine the concentration or presence of at least one analyte in a sample. At least one dendrimer-reagent preparation is made where each preparation comprises a plurality of dendrimer-reagent complexes, each complex having a specificity for at least two different analytes. The dendrimer-reagent preparation may also contain a plurality of dendrimer-reagent complexes having specificity for a single analyte. Effective amounts of the preparation or preparations are applied to a delimited area of a solid phase under conditions effecting immobilization of the dendrimer-reagent complexes on the solid phase. A sample is applied under binding conditions to the solid phase. A selected amount of an indicator or a labeled specific competitive reagent is added to the solid phase. The amount of indicator or label bound to the solid phase is determined and correlated to the concentration or presence of at least one analyte in the sample.

The complexes used in the methods described in the preceding paragraph comprise dendrimers coupled to reagents. The reagents can be, without limitation, antibodies or antibody fragments, specific binding proteins, or analytes. The sample and indicator can be applied simultaneously or sequentially to the solid phase.

The present invention also includes a method for immobilizing specific binding assay reagents with different analyte specificities on a solid phase. At least one dendrimer-reagent preparation is prepared containing a plurality of dendrimer-reagent complexes, each of the dendrimer-reagent complexes having a specificity for at least two different analytes. The dendrimer-reagent preparation may also contain a plurality of dendrimer-reagent complexes having specificity for a single analyte. The reagents can be, without limitation, antibodies, antibody fragments, specific binding proteins or analytes. The reagents are coupled to dendrimers by coupling methods that include but are not limited to the formation of carbon-sulfur (C-S) linkages.

The present invention includes a solid phase composition for use in a specific binding assay. The solid phase composition includes a solid phase comprising a mat of compressed fibers, and an analyte-binding component comprising at least one dendrimer-reagent preparations. Each preparation comprises a plurality of dendrimer-reagent complexes, each complex having a specificity for at least two different analytes. The dendrimer-reagent preparation may also contain a plurality of dendrimer-reagent complexes having specificity for a single analyte. The reagents can be, without limitation, antibodies, antibody fragments, specific binding proteins or analytes. The preparation is immobilized on a delimited area of the solid phase. The solid phase can be a glass fiber filter.

The present invention also includes articles of manufacture comprising packaging material and dendrimer-reagent preparations within the packaging material. The preparations may comprise a plurality of dendrimer-reagent complexes, each complex having a defined analyte specificity with the analyte specificities differing for each preparation. Alternatively, the preparation may comprise a plurality of dendrimer-reagent complexes where each of the dendrimer-reagent complexes has a specificity for at least two different analytes. The packaging material contains a label or package insert that indicates that the dendrimer-reagent preparations can be used in conducting specific binding assay methods described above.

DETAILED DESCRIPTION

The dendrimers most useful in preparing the solid phase supports of the present invention are generally spherical branched polymers having "star" configurations as disclosed in U.S. Pat. No. 4,507,466. The star configuration derives from a structured branching wherein individual branches radiate out from a nucleus, or core region. The polyvalent core is covalently bonded to at least two ordered dendritic (tree-like) branches that extend through at least two tiers, or generations. The outermost tier or generation may be derivatized to terminate in functional groups that may be chemically reactive with a variety of other molecules. Thus, star dendrimers are unitary molecular assemblages that possess three distinguishing architectural features, namely (a) an initiator core, (b) interior layers (generations) composed of repeating units radially attached to the initiator core, and (c) an exterior surface of terminal functionality attached to the outermost generation.

The size, shape and reactivity of a dendrimer can be controlled by the choice of the initiator core, the number of generations employed in creating the dendrimer, and the choice of the repeating units employed at each generation. Depending on the number of generations employed, dendrimers of discrete sizes are readily obtained. In addition, chemical modification of all or a portion of the surface moieties may create new surface functionalities appropriate for particular diagnostic or therapeutic operations. Generally spherical dendrimers of configurations suitable for use in the present invention are disclosed in U.S. Pat. No. 4,507,466 and U.S. Pat. No. 4,568,737. Alternatively, dendrimers of non-spherical configuration, such as those disclosed in U.S. Pat. No. 4,694,064, incorporated by reference herein, may be adapted for use in the present invention. Preferably, the dendrimers have an outer functionalized surface having amine-terminated functional groups. For example, an E5 dendrimer is a fifth-generation, ethylenediamine core particle having 128 amine-terminated end (surface) groups and a molecular weight of 28,826. The amine-terminated end groups impart a net positive charge to the surfaces of such dendrimers under normal assay conditions.

A variety of reliable and reproducible chemistries are available for attachment of specific binding assay reagents to the outer functionalized surfaces of dendrimers. For example, specific binding assay reagents may be attached to the dendrimers by the formation of carbon-sulfur (C-S) linkages by combining dendrimers derivatized with sulfosuccinimidyl-(4-iodoacetyl) aminobenzoate (sulfo-SIAB) with sulfhydryl-containing assay reagents. Alternatively, the specific binding assay reagents may be attached to the dendrimers by the formation of carbon-nitrogen (C-N) linkages or carbon-oxygen (C-O) linkages. See U.S. patent application Ser. No. 08/021,928, incorporated by reference herein. Dendrimer surface functional groups in addition to amino terminal groups include hydroxy, mercapto, carboxyl, alkenyl, allyl, vinyl, amido, halo, urea, oxiranyl, aziridinyl, oxazolinyl, imidazolinyl, sulfonato, phosphonato, isocyanato and isothiocyanato. Various known chemistries are usable with this wide range of surface functional groups and are useful for attachment of assay reagents to such functional groups.

Applicants have discovered that dendrimer-reagent complexes may be used for immobilization of reagents on a specific binding assay solid phase. While such complexes are useful for preparation of various solid phase reagents in immunoassays and other assays, the applicants have found a particularly useful application of such complexes in use with glass fiber filter substrates and radial partition assays. Radial partition immunoassay as disclosed in Giegel et al., Clin. Chem. 28:1894–98 (1982) and in U.S. Pat. No. 4,517,288 is an assay procedure in which all steps are conducted directly on a solid phase. Antibodies or other reagents are immobilized on a small area of glass fiber filter paper. Various calibrators containing known amounts of an analyte to be detected or various unknown samples potentially containing such an analyte are then allowed to react with this immobilized receptor. Following appropriate additions of labeled analogues or other labeling reagents, excess reagents are removed from the center area of the filter paper by application of a wash fluid. In the case of an enzyme immunoassay, the wash fluid may contain the substrate for the enzyme, thus initiating the enzyme reaction simultaneously with the wash step. Preferably the action of the enzyme on the substrate generates a fluorescent signal. The enzyme activity in a part of the center area is then quantifiable by front-surface fluorometry. Depending on the assay format, i.e., direct binding assay or competitive assay, the rate of fluorescence is directly or inversely proportional to the concentration of analyte in the sample.

As described above, it is preferred that the solid phase present a relatively "inert" surface. That is, the surface should be relatively nonreactive with biological materials, particularly with respect to nondiscriminate adsorption of proteinaceous materials. In the preferred embodiments of this invention, the physical form of the solid phase is such that the interstices or pores within the solid phase are sufficiently small so that the reaction fluids are retained and transported by capillary action. On the other hand, the solid phase pores or interstices should not be so small so as to retain undesirable components that might give rise to false positive signals.

The solid phase is advantageously composed of a mat of compressed fibers, such as glass or synthetic fibers or relatively inert cellulosic materials. The solid phase also may be constructed of other porous constituents such as sintered glass, ceramics and synthetic polymeric materials. Glass fiber filter paper is the preferred solid support of the present invention because of its inert characteristic and because of its ability to adsorb the soluble complexes of this invention in quantities sufficient for quantitative evaluation of retention of assay reagents. The surfaces of the glass fibers may carry a net negative charge, which facilitates adsorption of dendrimers having substantially positively charged surfaces under assay conditions, i.e., dendrimers with amine terminal surface groups.

The dendrimer-reagent complexes of this invention, once adsorbed onto a suitable solid phase, can be used in a wide variety of analytical protocols for analysis of a variety of biological materials. For example, dendrimer-receptor complexes may be useful for immunoassay of blood or urine for the presence of therapeutic drugs, natural or synthetic steroids, hormones, enzymes, antibodies and other analytes of interest.

Therapeutic agents that can be analyzed in such protocols include without limitation digoxin, dilantin, phenobarbital, theophylline, gentamicin, quinidine, and the like. Solid phases prepared in the foregoing manner can also be used in immunoassays for the detection of steroids such as cortisol, aldosterone, testosterone, progesterone, and estriol or serum protein such as ferritin. Hormone levels are also capable of determination through the use of solid phase complexes of the present invention. These hormones include without limitation thyroid hormones such as tetraiodo- and triiodo-thyronine and thyroid stimulating hormone (TSH); peptide hormones such as insulin, corticotropin, gastrin, angiotensin, and proangiotensin; and polypeptide hormones such as thyrotropin, levteotropin, somatotropin and human chorionic gonadotropic hormone (HCG). Other applications of the complexes of the present invention include assay of relatively small molecules involved in metabolism, i.e., folate, to assay of polypeptide antigens and antibodies associated with infectious disease, i.e., antigens and antibodies associated with HIV, hepatitis, CMV, syphilis, Lyme disease agents, and numerous other infectious agents.

Assay reagents such as receptors may be coupled to the dendrimers via SIAB linkage or other methods and then applied to solid phase materials such as glass fiber filters. In a preferred embodiment, "tabs" as marketed by Baxter Diagnostics Inc. are assembled from GF/F glass filter paper distributed by Whatman Inc. and snap-fit plastic tab parts as discussed below. Generally the dendrimer-reagent complexes are applied to the center areas of such tabs in an appropriate buffer solution. Generally such buffers should include surfactants, analyte-free serum albumin and a preservative such as sodium azide. Aliquots of dendrimer complex solution are spotted onto the centers of blank tabs, then oven dried with heat. After cooling, the tabs may be stored under refrigeration.

In an alternative embodiment, the dendrimers themselves may be formed into a solid phase. The dendrimers may be dissolved in appropriate solvents and sprayed or otherwise applied to appropriate solid surfaces. Upon evaporation of the solvent, the dendrimers become concreted into thin films or filaments and can be so isolated. Alternatively, such thin films of concreted dendrimers can be used to coat the internal surfaces of tubes or other containers used in specific binding assays. Assay reagents such as antibodies can be covalently coupled to such dendrimer concretions either before or after application of the sprayed material and subsequent drying period.

The dendrimer-reagent complex/solid phase preparations of the present invention are applicable to a variety of specific binding assay formats. For example, various direct-binding assays may be employed with these reagents. In such assays, receptors such as antibodies or binding proteins are covalently coupled to the dendrimers and immobilized on the solid phase. The immobilized dendrimer-receptor complexes are contacted with a sample containing the analyte of interest. Following binding of the analyte by the immobilized receptor, the solid phase is washed and then contacted with an indicator. The term "indicator" in the context of this invention means a labeled conjugate. The conjugate comprises an antibody, antibody fragment, binding protein or analyte depending on assay format, and the label is a fluorescent, enzymatic, colorimetric, radiometric or other labeling molecule that is associated either directly or indirectly with the conjugate. The label may comprise an enzymatic compound that produces fluorescence upon contact with a substrate. The extent to which the indicator is present on the solid support can be correlated with the amount of unknown analyte as disclosed, for example, in Tijssen, P., *Laboratory Techniques in Biochemistry and Molecular Biology,* Practice and Theory of Enzyme Immunoassay, pp. 173–219 (Chapter 10) and pp. 329–384 (Chapter 14), Elsevier Science Publishers, Amsterdam, The Netherlands, 1985.

The dendrimer/reagent complexes also may be used in competitive assay formats. In such formats, the solid phase containing immobilized receptor or other molecule with specificity for a selected analyte is contacted with a sample presumably containing such analyte and with a specific competitive reagent. The specific competitive reagent may be a labeled analogue of the analyte. In this embodiment, the labeled analogue competes with the sample analyte for binding to a receptor immobilized on the solid phase. In an alternative embodiment, analyte may be coupled to a solid phase and contacted with a sample and with a specific competitive reagent, for example a labeled receptor for the analyte. In this format, sample analyte competes with solid phase analyte for binding with soluble labelled receptor. In both embodiments, the amount of label bound to the solid phase after washing provides an indication of the levels of analyte in the sample. That is, the amount of label bound to the soluble phase is inversely proportional to the amount of analyte in the sample.

Various instruments are available for applying the dendrimer-reagent conjugates and various other binding assay reagents to a solid phase, washing, and reading the amounts of indicator bound to the solid phase. In a preferred embodiment, the solid phase comprises the glass fiber filter tabs as described above, and the instrument comprises the Stratus® Immunoassay System, available from Baxter Diagnostics Inc. This instrument is a batch-processing bench-top instrument, described by Giegel et al., Clin. Chem. 28:1894–98 (1982). The instrument is adapted to process tabs in the radial partition immunoassay format, which format is also described in Giegel et al. The instrument includes fluid dispensers for sample, conjugate and substrate washes. Microprocessor-controlled stepping motors aspirate and dispense required aliquots of reagents. All timing and operational aspects of the dispensers are predetermined by a program routine within the analyzer. The instrument also includes a tab transport system, heated platens with temperature monitoring, sample and reagent fluid pumps, a read station, data processing, and means for tab disposal. For quality control, the instrument microprocessor control program periodically verifies critical operating conditions such as reference voltages, temperatures, and dispensing settings, and flags for out-of-limit values.

In the present invention, Applicants have developed a solid phase that contains a population of dendrimer-reagent complexes with specificity for at least two different analytes. That is, the solid phase contains at least two different dendrimer-reagent preparations, each preparation having specificity for a selected analyte. Moreover, the dendrimer-reagent complexes of the preparations are intermixed in a delimited area of the solid phase to form a reaction zone useful for analysis of multiple analytes.

The present invention overcomes several deficiencies in the currently available random access systems including relatively expensive individual packaging and relatively long assay times. The present invention is useful for analysis of a plurality of analytes. The mixed solutions of the present invention are especially useful in cases where a patient sample is to be assayed for a specific diagnosis using a panel of tests where each test of the panel is an indication of a different stage of a clinical symptom. For example, a cardiac panel might require testing for creatine kinase isozyme MB (CKMB), Troponin, Myoglobin and Digoxin and a cancer markers panel might test for carcinoembryonic antigen (CEA), alpha-fetoprotein (AFP) and human chorionic gonadotropin hormone (HCG).

The invention will be further understood with reference to the following illustrative embodiments, which are purely exemplary, and should not be taken as limiting the true scope of the present invention as described in the claims.

EXAMPLE 1

Preparation of Solid Phase Supports (Tabs)

Solid phase supports used in the present experiments comprised "tabs" as used with the Stratus® analyzer instrument or the Stratus® II analyzer instrument, both marketed by Baxter Diagnostics Inc. These tabs are assembled from 1-in. (2.5 cm)-wide rolls of GF/F glass filter paper (Whatman Inc.) and snap-fit plastic tab parts, as disclosed in Giegel et al., Radial Partition Immunoassay, Clin. Chem. 28:1894–98 (1982). Appropriate concentrations of dendrimer solutions, antibody solutions or other protein or control solutions are made up in spotting buffer. The spotting buffer composition may be varied to accommodate particular experimental or manufacturing parameters. Generally the spotting buffer may comprise, for example, an appropriate buffer including but not limited to 20 mM-200 mM Tris, pH 7.0–9.0, a non-ionic surfactant such as Zonyl® FSN (E.I. DuPont DeNemours & Co., Cat. No. CH 7152S) in a concentration range of 0.1%–1.0%, bovine serum albumin (BSA) at 0.5%–10.0% and 0.1% sodium azide. Preferably the spotting buffer comprises 30–100 mM Tris, pH 7.0–8.5, 0.1%–0.5% Zonyl® FSN, 1.0%–3.0% BSA and 0.1% sodium azide. Most preferably the spotting buffer comprises 50 mM Tris, pH 8.0, 0.1% Zonyl® FSN, 2.0% BSA and 0.1% sodium azide. Fluorinated surfactants (e.g. 3M Cat. No.'s FC 171 and FC 170C) and other appropriate surfactants known to the skilled artisan may be substituted for Zonyl® FSN.

Aliquots of 76 μl of a selected solution are spotted onto the centers of blank tabs, which are then oven-dried at 80°–90° C. After cooling, the tabs may be stored at 2°–8° C. until used. Spotting of the solutions on the tabs may be carried out manually with a pipetting device or may be carried out with automated manufacturing procedures. Alternatively, the tabs may be spotted and processed by the Stratus® II instrument itself, following appropriate programming of machine parameters to apply selected aliquots of stock solutions to the centers of tabs.

EXAMPLE 2

General Procedure for Coupling of Antibodies to Derivatized Dendrimers

A one-fifth volume of a 0.5 M sodium phosphate buffer, pH 7.0, was added to an aqueous solution containing approximately 2% by weight (containing about $4 \times 10^{17}$ particles) of E5 dendrimers (ethylenediamine core, fifth generation, estimated diameter of 70 Å from Michigan Molecular Institute, Midland, Mich.). The pH of the solution was adjusted to 7.6. A freshly prepared solution of 20 mg/ml sulfo-SIAB (Pierce) was added with constant mixing to the dendrimer solution at about a 10 to 25:1 molar challenge ratio (sulfo-SIAB:Dendrimer). The mixture was incubated at 30° C. for one hour and then loaded onto a G-25 column prepared and eluted with 0.1 M sodium acetate, pH 4.5. The first peak eluted from the column, as detected by absorption at 280 nm, contains the derivatized dendrimers. The solution containing the derivatized dendrimers was collected and either stored in an ice bath for no more than 12 hours prior to its use or stored frozen at −10° C. for up to two weeks.

A solution of 5.0 mg/ml of the desired antibody in a reduction buffer (0.1 M sodium phosphate-5.0 mM EDTA, pH 6.0) was prepared and incubated for 10 minutes at 37° C. Dithiothreitol (DTT) was dissolved in reduction buffer at a concentration of 11.4 mg/ml. The DTT solution was added to the antibody solution in a volume equal to ⅑ of the volume of the antibody solution and then incubated at 37° C. for an additional hour. Excess DTT was removed by passing the solution through a G-25 column that had been prepared and eluted with the reduction buffer. Pooled protein fractions containing IgG-SH were stored at 2–8° C. until coupled with the iodoacetylated dendrimer.

The iodoacetylated dendrimer solution and the reduced antibody solution representing a 3:1 molar challenge ratio of dendrimer to antibody were mixed and the dendrimer/antibody solution was buffer exchanged with 0.1 M sodium phosphate, pH 7.6. This mixture was adjusted to a protein concentration of 5.0 mg/ml and was incubated at 2–8° C. for 16 hours. Excess thiol groups were quenched by adding 20 μl of a solution of 10 mg/ml N-ethylmaleimide in N,N-dimethylformamide (DMF) for each milliliter of the reaction mixture. The resulting reaction mixture was incubated at ambient temperature for 1 hour. Purification of the dendrimer-coupled antibody complex was carried out on a gel filtration column (AcA-44 from IBF-Sepracor) prepared and eluted with a buffer containing 10 mM sodium phosphate, 2.7 mM KCl, 120 mM NaCl and 0.1% azide, pH 7.4 (PBS). The main protein peak eluted from the column was collected, filtered through a 0.22 μm filter and stored at 2–8° C. Protein concentration was determined using the BCA test (Pierce Chemical Company).

EXAMPLE 3

Coupling of Anti-hTSH Antibody (CA2) with Dendrimers

About 12 ml of ascites fluid containing approximately 60 mg of anti-hTSH (CA2) antibody was purified over a Q-Sepharose column (1.0×13.0 cm) using a gradient between 20 mM Tris, pH 8.5 and 20 mM Tris/0.3 M NaCl, pH 7.0 to yield 54 mg of the purified antibody protein. CA2 is on deposit at the American Type Culture Collection (ATCC) under Accession Number 1437. The antibody solution, containing 35 mg protein, was diluted with an equal volume of binding buffer (Bio-Rad) and purified over a Protein A column (1.0×6.5 cm, Bio-Rad AffiPrep) by absorbing the antibody to the column and then eluting the bound protein with 0.1 M sodium acetate-0.1 M sodium chloride, pH 5.0 to yield 26.0 mg of the antibody in solution.

The E5 dendrimer was iodoacetylated following the general procedure discussed in Example 2 above. A 20-fold molar excess of sulfo-SIAB was added to the aqueous dendrimer solution. Each dendrimer particle incorporated approximately 2.5 iodoacetyls.

The antibody solution (2.0 ml at 5.0 mg/ml) was reduced for 1 hour at 37° C. with DTT (0.23 ml of 4.5 mg/ml) in 0.1 M sodium phosphate-5.0 mM EDTA, pH 6.5 following the general procedure given in Example 2 above. After desalting over a G-25 column in the reduction buffer, the product showed the presence of about 10 sulfhydryls per IgG.

The reduced antibody was then coupled with the iodoacetylated dendrimer in a 1:3 molar ratio as described in the general coupling procedure set out in Example 2 above. Final product was purified either by FPLC using a Superdex 200 (1.6×60.0 cm; Pharmacia) column or by using an AcA-44 column in PBS. The stoichiometry of dendrimer to antibody in the final purified product was found to be 1.0±0.3.

EXAMPLE 4

Coupling of Anti-CKMB Antibody with Dendrimer

Purification of the antibody (Conan, American Type Culture Collection Accession No. HB8939) was carried out over Q-Sepharose as described above in Example 2, producing about a 65% yield. The E5 dendrimer was challenged with a 20-fold molar excess of sulfo-SIAB to incorporate approximately 2.5 iodoacetyls per dendrimer. After desalting over a G-25 column in the reduction buffer, the product showed the presence of about 8.5 sulfhydryls per IgG. Coupling of the derivatized E5 with the reduced IgG was carried out as described in the case of hTSH (Example 3). Purification of the final product was carried out over an AcA-44 column prepared and eluted with PBS.

EXAMPLE 5

Coupling of Anti-T4 Antibody with Dendrimer

Coupling of the derivatized E5 with the reduced antibody (Medix Biochem, Cat. No. MIT 0501) was carried out as described in the general procedure for coupling, set out in Example 2. The reduced IgG showed the presence of about 7.8 sulfhydryls per IgG. Purification of the complex was carried out on an AcA-44 column; the complex was eluted with PBS.

EXAMPLE 6

Preparation of Mixed Solution of Several Dendrimer-Coupled Antibodies

A mixed dendrimer spotting buffer solution containing three dendrimer-coupled antibodies, i.e., antibodies against CKMB, hTSH and T4, was prepared. The optimized dendrimer spotting diluent consisted of 50 mM Tris, 0.1% v/v Zonyl® FSN, and 0.18% w/v unmodified E5 at pH 8.0. This diluent was used for the three E5 complex mixtures. The spotting buffer and optimum concentration for the T4-E5 complex was first optimized prior to mixing it with the other two analyte complexes (hTSH and CKMB). It was essential that the formulation of the T4 complex diluent was optimized using T4-E5 without the presence of the other two complexes. The final working concentrations of each complex, in dendrimer spotting buffer, was determined to be 0.56 μg/ml for T4-E5, 10 μg/ml for hTSH-E5 and 10 μg/ml for CKMB-E5. Therefore, 2 ml solutions of each complex at 3 times the optimum working concentrations, in the dendrimer spotting diluent, were prepared: 1.68 μg/ml for T4-E5, 30 μg/ml for CKMB-E5 and 30 μg/ml for hTSH-E5. The solutions were then mixed together, incubated overnight, and tested on the Stratus® II analyzer.

EXAMPLE 7

Evaluation of a Mixture of Three Types of Dendrimer-Coupled Antibodies on Stratus II®

A stock solution of the dendrimer-coupled specific antibodies was diluted in a solution containing 50 mM Tris, 0.1% v/v Zonyl® FSN, 0.18% w/v unmodified E5 at pH 8.0 (spotting buffer) to a known concentration of about 0.02–0.15% of the unmodified dendrimer. A fixed volume of this solution was spotted onto tabs as described in Example 1 above. A direct specific binding assay was performed utilizing calibrated or variable sample amounts of CKMB, hTSH or T4 as analytes. A known volume of the calibrator or the sample and the mixture was applied to a tab. After an appropriate interval, the specific alkaline phosphate conjugate and the substrate wash were applied sequentially to the tab and the signal thus generated was measured by front surface fluorometry in a Stratus® instrument, as described in Giegel et al., Clin. Chem 28:1894–98 (1982). For detection of T4, the sample was preincubated with the releasing buffer containing aminonaphthalene sulfonic acid and then mixed with the dendrimer-coupled antibody solution. The remaining steps followed the general assay procedure.

The radial partition assay format described in Giegel et al. was used in all of the experiments. Calibrator solutions A, B, C, D, E and F were prepared either in normal human serum or in a Tris-buffered solution (pH 7.5) including BSA, stabilizer and 0.1% sodium azide as a preservative. Calibrator solutions A, B, C, D, E and F for hTSH contained concentrations of 0, 0.25. 0.75, 3, 12 and 50 μIU/ml, respectively; the calibrator solutions for CKMB contained concentrations of 0.0, 4.80, 11.60, 26.90, 61.10 and 127.80 ng/ml; and the calibrator solutions for T4 contained concentrations of 0.0, 2.5, 5.0, 10.0, 15.0 and 25.0 μg/dl.

The assay was performed on the Stratus® II instrument by aspirating and delivering 76 μl of a preincubated mixture of 132 μl of a selected calibrator (or sample) and 38 μl of the E5-coupled antibody onto a blank tab. Twenty μl of the appropriate alkaline phosphatase conjugate (0.75 μg/ml) were then delivered to each tab. The Stratus® instrument substrate probe then aspirated 70 μl of the substrate wash (pH 9.0 Tris buffer containing 1.0 mM 4-methylumbelliferyl phosphate, alkaline phosphatase inhibitor, stabilizers, blue dye, surfactant and 0.1% sodium azide) and released 20 μl and 50 μl sequentially to the tab. As soon as the second substrate wash was delivered, the initial fluorescence rates were read and recorded in the instrument memory.

The amount of fluorescence generated by action of the phosphatase on the methylumbelliferyl phosphate substrate was detected by the Stratus® instrument and converted to a "rate" expressed in voltage per unit time, which is presented in the Tables as mV/min ("Stratus Rates"). The Stratus rate is a measure of the intensity of the fluorescence, which is, in turn, a measure of the amount of analyte bound to the reactive portion of the tab.

During a Stratus® instrument run, the fluorescence rates of individual calibrators are measured and the values directed to storage locations in a microprocessor memory. After all calibrators have been measured, the program calculates "Rodbard" parameters A, B, C and D (Davis, S. E. et al., J. Immunoassay 1:15–25 (1980)) using a multi-pass linear regression routine that fits a mathematical relationship to the measured data points in the form shown in the following equation:

$$R = \{(A-D)/[1+B(X/C)]+D\}$$

where R is the fluorescence rate and X is the corresponding concentration. The equation is a generalized sigmoidal curve that has been reported to give an excellent fit in various immunoassay systems. Based on the resulting A, B, C and D parameters stored in the memory, the instrument provides the concentration readout for the samples assayed.

Table 1 shows data from full calibration runs. Within sensitivity of the Stratus® system, rates for the three analytes were not affected by the presence of non-specific dendrimer-coupled antibody. This conclusion is confirmed by results obtained with three normal human serum-based controls (Table 1). The controls were prepared by spiking known levels of the particular analyte into normal human serum. The three controls represent the analyte concentration in three different parts of the calibration curve.

TABLE 1

DETECTION OF CKMB, hTSH AND T4 USING EITHER A SINGLE DENDRIMER-COUPLED ANTIBODY OR A MIXTURE OF ALL THREE DENDRIMER-COUPLED ANTIBODY SOLUTIONS*

| Cal | CKMB** SINGLE | CKMB** MIXTURE | hTSH** SINGLE | hTSH** MIXTURE | T4^^ SINGLE | T4^^ MIXTURE |
|---|---|---|---|---|---|---|
| A | 165.2 | 155.3 | 108.0 | 116.6 | 9139.9 | 9075.1 |
| B | 576.2 | 563.7 | 202.4 | 186.7 | 5323.4 | 5413.1 |
| C | 1231.4 | 1150.4 | 359.4 | 363.9 | 3324.8 | 3421.7 |
| D | 2717.9 | 2648.3 | 1157.1 | 1145.0 | 2000.4 | 2019.3 |
| E | 5653.5 | 5798.9 | 3947.4 | 4120.7 | 1479.6 | 1503.9 |
| F | 10507.1 | 10291.6 | 13948.5 | 14139.1 | 1107.8 | 1102.1 |
| CONTROLS: | | | | | | |
| I | 4.57 | 4.53 | 1.44 | 1.49 | 2.73 | 2.87 |
| II | 18.3 | 19.1 | 11.3 | 11.1 | 3.6 | 4.2 |
| III | 31.8 | 31.3 | 30.6 | 28.3 | 8.0 | 8.6 |

TABLE 1-continued

DETECTION OF CKMB, hTSH AND T4 USING EITHER A SINGLE DENDRIMER-COUPLED ANTIBODY OR A MIXTURE OF ALL THREE DENDRIMER-COUPLED ANTIBODY SOLUTIONS*

| Cal | CKMB** SINGLE | CKMB** MIXTURE | hTSH** SINGLE | hTSH** MIXTURE | T4^^ SINGLE | T4^^ MIXTURE |
|---|---|---|---|---|---|---|
| RODBARD PARAMETERS: | | | | | | |
| A | 165.6 | 155.3 | 107.9 | 116.6 | 9139.8 | 9075.1 |
| B | 1.0817 | 1.124 | 0.9875 | 1.0646 | 1.366 | 1.3909 |
| C | 289.73 | 206.22 | 210.14 | 102.227 | 2.852 | 2.994 |
| D | 35605.64 | 27551.02 | 69993.15 | 44251.59 | 692.37 | 688.81 |

*Numbers presented in the Table represent an average of duplicates; numbers for the calibration runs are given in mV/min.; numbers for the controls are given as ng/ml for CKMB assays, μIU/ml for hTSH assays, and μg/dL for T4 assays.
**10 μg/ml of the dendrimer-coupled antibody either separately or in the mixture.
^^0.56 μg/ml of the dendrimer-coupled antibody either separately or in the mixture.

Table 2 shows comparative data for a single sample detected either with a solution containing a single type of dendrimer-coupled antibody or with a solution containing a mixture of three types of dendrimer-coupled antibodies. A sample was prepared containing a 1:1 mixture of two human serum-based controls. The detected concentration of each of the three analytes was very similar whether the dendrimer-coupled antibody solution contained only a single type of dendrimer-coupled antibody or if the antibody solution contained a mixture of dendrimer-coupled antibodies.

TABLE 2

RANDOM DETECTION OF MULTIPLE ANALYTES IN A SINGLE SAMPLE WITH A SINGLE TYPE OF DENDRIMER-COUPLED ANTIBODY OR A MIXTURE CONTAINING THREE TYPES OF DENDRIMER-COUPLED ANTIBODIES

| | CKMB SINGLE | CKMB MIXTURE | hTSH SINGLE | hTSH MIXTURE | T4 SINGLE | T4 MIXTURE |
|---|---|---|---|---|---|---|
| MV/MIN* | 1321.4 | 1461.3 | 3842.8 | 3806.9 | 1944.2 | 2223.4 |
| CONC.^ | 12.62 | 14.26 | 11.44 | 10.79 | 9.73 | 8.88 |

*Average of triplicates.
^A Concentration determined from MV/MIN. Analyte concentration units are ng/ml, μIU/ml and μg/dl for CKMB, hTSH and T4 respectively.

EXAMPLE 8

Evaluation of a Mixture of Two Types of Dendrimer-Coupled Antibodies on Stratus II®

A mixed solution containing two dendrimer-coupled antibodies, i.e., antibodies against CKMB and hTSH, was prepared. The dendrimer spotting buffer consisted of 8.9% w/v BSA, 0.45% v/v Zonyl® FSN and 0.089% w/v E5, pH 8.0. The final working concentrations for the two-antibody mix was 10 μg/ml E5-CKMB complex and 10 μg/ml E5-hTSH complex. A fixed volume of this solution was spotted onto tabs as described in Example 1 above. A direct specific binding assay was performed using calibrated or variable sample amounts of CKMB or HTSH as analytes as in Example 7 above. Table 3 shows data from full calibration runs. Within sensitivity of the Stratus® system, rates for the two analytes were not affected by the presence of non-specific dendrimer-coupled antibody.

TABLE 3

DETECTION OF CKMB AND hTSH USING EITHER
A SINGLE DENDRIMER-COUPLED ANTIBODY OR A
MIXTURE OF TWO DENDRIMER-COUPLE ANTIBODIES*

| Cal | CKMB** | | hTSH** | |
|---|---|---|---|---|
| | SINGLE | MIXTURE | SINGLE | MIXTURE |
| A | 145.1 | 149.2 | 94.4 | 82.8 |
| B | 679.4 | 677.3 | 153.6 | 142.1 |
| C | 1490 | 1497.8 | 251.6 | 255.3 |
| D | 3280.4 | 3320.9 | 800 | 786.7 |
| E | 6914.4 | 6903.6 | 2933.9 | 2879.2 |
| F | 11683.2 | 12028.7 | 10180.2 | 9959.1 |
| CONTROLS**: | | | | |
| I | 4 | 4 | 1.13 | 1.15 |
| II | 16.1 | 16.1 | 9.04 | 9.01 |
| III | 26.6 | 27.4 | 21.21 | 20.58 |
| RODBARD PARAMETERS: | | | | |
| A | 145.148 | 149.195 | 94.397 | 82.751 |
| B | 1.105 | 1.094 | 1.027 | 1.013 |
| C | 164.415 | 192.828 | 176.896 | 186.455 |
| D | 26886.8 | 30651.4 | 47012.25 | 47369.68 |

*Average of duplicates. Numbers for the calibration runs are given in mV/min.; numbers for the controls are given as ng/ml for CKMB and μIU/ml for hTSH.
**5 μg/ml of the dendrimer-coupled antibody either separately or in the mixture.

EXAMPLE 9

Preparation of Multiple-Specificity Dendrimers

Dendrimers in which individual particles are coupled to more than one type of antibody may be prepared. The following are procedures for the production of antibody-coupled dendrimers in which individual dendrimer particles are coupled to anti-CKMB and anti-hTSH antibodies, or to anti-CKMB, anti-hTSH and anti-T4 antibodies. The dendrimers are iodoacetylated following the general procedure discussed in Example 2 above. A 20 to 50 fold molar excess of sulfo-SIAB is added to the aqueous dendrimer solution. Each dendrimer particle incorporates approximately 6–10 iodoacetyls.

A mixture of purified anti-CKMB and anti-hTSH antibodies in 1:1 ratio (by weight) is reduced for one hour at 37° C. with DTT in the reduction buffer following the general procedure described in Example 2 above. For coupling of anti-CKMB, anti-hTSH and anti-T4 a mixture of the three antibodies at a mass ratio of 18:18:1 is utilized prior to reduction. After desalting over a G-25 column that is prepared and eluted with the reaction buffer, the product will show the presence of about 10 sulfhydryls per IgG.

The reduced antibody mixture is then coupled to the iodoacetylated dendrimer in a 1:5 to 1:10 molar ratio as described in the general coupling procedure set out in Example 2 above. The excess uncoupled antibody present in the final product solution is removed by gel filtration purification either by using an AcA-34 (or equivalent) column or on FPLC using a Superdex 200 (Pharmacia) column in PBS. The fractions containing IgG-E5 are pooled and the protein concentration is determined by BCA assay. In cases where a mixture of anti-T4, anti-CKNB and anti-hTSH is used for coupling, the dendrimer-coupled antibody solution is diluted to 20.6 μg/ml in 50 mM Tris, 0.1% FSN, 0.1% azide, pH 8.0 and tested on Stratus® II. The dendrimer-coupled antibody solution prepared from a mixture of anti-CKMB and anti-hTSH antibodies is diluted to 20 μg/ml in 50 mM Tris, 2% BSA, 0.1 % FSN, and 0.1% azide, pH 8.0 for testing and storage.

The above procedures can be modified to suit particular assay conditions. For example, higher generation dendrimers and dendrimers with COOH or SH terminal functional groups can be used. Alternatively, dimerized or polymerized forms of E5 or other dendrimers can be employed. Further, levels of iodoacetylation can be readily adjusted to optimize coupling conditions involving different reagents.

The foregoing detailed description has been provided for a better understanding of the invention only and no unnecessary limitation should be understood therefrom as some modifications will be apparent to those skilled in the art without deviating from the spirit and scope of the appended claims.

What is claimed is:

1. A method for conducting a specific binding assay to determine the concentration or presence of one or more analytes or receptors for said analytes in a sample, comprising the steps of:
    (a) applying said sample to a delimited area of a solid phase having interstices therein, said delimited area having effective amounts of at least two types of immobilized dendrimer-reagent complexes, each said dendrimer-reagent complex comprising a dendrimer covalently coupled, prior to immobilization, to a specific binding assay reagent, said reagent having a defined analyte specificity, said specificity differing for each said type of dendrimer-reagent complex, said sample applied under conditions effecting binding of said one or more analytes or receptor of said one or more analytes to said reagent, said solid phase with immobilized dendrimer-reagent complexes having interstices;
    (b) applying a selected amount of one or more labeled conjugates to said delimited area under conditions effecting binding of each said conjugate to a corresponding one of said analytes or a receptor of said one analyte;
    (c) determining the amount of each said conjugate bound to said corresponding analyte or receptor of said corresponding analyte on said delimited area; and
    (d) correlating said amount of each said conjugate with the concentration or presence of said corresponding analyte or receptor of said corresponding analyte in said sample.

2. The method of claim 1, wherein said reagents are selected from the group consisting of antibodies, antibody fragments, specific binding proteins and analytes.

3. The method of claim 1, wherein said delimited area has two types of dendrimer-reagent complexes.

4. The method of claim 1, wherein said delimited area has three types of dendrimer-reagent complexes.

5. The method of claim 1, wherein said sample and said labeled conjugate are applied simultaneously to said solid phase.

6. A method for conducting a specific binding assay to determine the concentration or presence of one or more analytes or receptors for said analytes in a sample, comprising the steps of:
    (a) applying said sample to a delimited area of a solid phase having interstices therein, said delimited area having effective amounts of at least two types of immobilized dendrimer-reagent complexes, each said dendrimer-reagent complex comprising a dendrimer covalently coupled, prior to immobilization, to a specific binding assay reagent, said reagent having a defined analyte specificity, said specificity differing for each said type of dendrimer-reagent complex, said sample applied under conditions effecting binding of said one or more analytes or receptor of said one or more analytes to said reagent, said solid phase with immobilized dendrimer-reagent complexes having interstices;

(b) applying a selected amount of one or more labeled specific competitive reagents to said delimited area, each said competitive reagent corresponding to one of said analytes or a receptor of said one analyte, under conditions effecting binding of each said competitive reagent to at least one of said complexes;

(c) determining the amount of each said competitive reagent bound to said complexes on said delimited area; and (d) correlating said amount of each said competitive reagent with the concentration or presence of said corresponding analyte or receptor of said corresponding analyte in said sample.

7. The method of claim 6, wherein said specific competitive reagent is a labeled analogue of said at least one analyte.

8. The method of claim 6, wherein said specific competitive reagent is a labeled receptor for said at least one analyte.

9. The method of claim 6, wherein said reagents are selected from the group consisting of antibodies, antibody fragments, specific binding proteins and analytes.

10. A method for immobilizing a plurality of specific binding assay reagents on a solid phase, comprising the steps of:

(a) preparing at least two types of dendrimer-reagent complexes, each said complex comprising a dendrimer covalently coupled, prior to immobilization, to a specific binding assay reagent, said reagent having a defined analyte specificity, said specificity differing for each said type of dendrimer-reagent complex; and (b) adding effective amounts of said types of said dendrimer-reagent complexes to a solid phase having interstices therein under conditions effecting immobilization of said complexes on a delimited area of said solid phase, said solid phase retaining said interstices after adding said dendrimer-reagent complexes.

11. The method of claim 10, wherein said types of said complexes are mixed together prior to being added to said solid phase.

12. The method of claim 10, wherein said reagents are selected from the group consisting of antibodies, antibody fragments, specific binding proteins and analytes.

13. The method of claim 10, wherein said covalently coupling of said reagent to said dendrimer is by C-S linkage carried out by combining SIAB-labeled moieties with sulfhydryl-containing moieties.

14. A solid phase composition for use in a specific binding assay, comprising (a) a solid phase having interstices therein; and (b) an analyte-binding component comprising at least two types of dendrimer-reagent complexes, each said complex comprising a dendrimer covalently coupled to a specific binding assay reagent, said reagent having a defined analyte specificity, said specificity differing for each said type of dendrimer-reagent complex, said complexes being immobilized within a delimited area of said solid phase, said solid phase composition having interstices.

15. The solid phase composition of claim 14, wherein said reagents are selected from the group consisting of antibodies, antibody fragments, specific binding proteins and analytes.

16. The solid phase composition of claim 14, wherein said analyte-binding component comprises two types of said complexes.

17. The solid phase composition of claim 14, wherein said analyte-binding component comprises three types of said complexes.

18. The solid phase composition of claim 14, wherein said solid phase comprises a mat of compressed fibers.

19. A method for conducting a specific binding assay to determine the concentration or presence of one or more analytes or receptors for said analytes in a sample, comprising the steps of:

(a) applying said sample to a delimited area of a solid phase having interstices therein, said delimited area having effective amounts of at least one type of immobilized dendrimer-reagent complex, each said complex comprising a dendrimer covalently coupled to at least two specific binding assay reagents, each said reagent having a defined analyte specificity, said specificity differing for each said reagent, said sample applied under conditions effecting binding of said one or more analytes or receptor of said one or more analytes to said reagent said solid phase retaining said interstices after said application of said dendrimer-reagent complexes;

(b) applying a selected amount of one or more labeled conjugates to said delimited area under conditions effecting binding of each said conjugate to a corresponding one of said analytes or a receptor of said one analyte;

(c) determining the amount of each said conjugate bound to said corresponding analyte or receptor of said corresponding analyte on said delimited area; and (d) correlating said amount of each said conjugate with the concentration or presence of said corresponding analyte or receptor of said corresponding analyte in said sample.

20. The method of claim 19, wherein each said type of said complex has specificity for a single analyte or a receptor of said single analyte.

21. The method of claim 19, wherein said reagents are selected from the group consisting of antibodies, antibody fragments, specific binding proteins and analytes.

22. The method of claim 19, wherein said sample and said labeled conjugate are applied simultaneously to said solid phase.

23. A method for conducting a specific binding assay to determine the concentration or presence of one or more analytes or receptors of said analytes in a sample, comprising the steps of:

(a) applying said sample to a delimited area of a solid phase having interstices therein, said delimited area having effective amounts of at least one type of immobilized dendrimer-reagent complex, each said complex comprising a dendrimer covalently coupled, prior to immobilization, to at least two specific binding assay reagents, each said reagent having a defined analyte specificity, said specificity differing for each said reagent, said sample applied under conditions effecting binding of said one or more analytes or receptor of said one or more analytes to said reagent, said solid phase with immobilized dendrimer-reagent complexes having interstices;

(b) applying a selected amount of one or more labeled specific competitive reagents to said delimited area, each said competitive reagent corresponding to one of said analytes or a receptor of said one analyte, under conditions effecting binding of each said competitive reagent to at least one of said complexes;

(c) determining the amount of each said competitive reagent bound to said complexes on said delimited area; and (d) correlating said amount of each said competitive reagent with the concentration or presence of said corresponding analyte or receptor of said corresponding analyte in said sample.

24. The method of claim 23, wherein each said type of said complex has specificity for a single analyte or a receptor of said single analyte.

25. The method of claim 23, wherein said specific competitive reagent is a labeled analogue of said at least one analyte.

26. The method of claim 23, wherein said specific competitive reagent is a labeled receptor for said at least one analyte.

27. The method of claim 23, wherein said reagents are selected from the group consisting of antibodies, antibody fragments, specific binding proteins and analytes.

28. A method for immobilizing a plurality of specific binding assay reagents on a solid phase, comprising the steps of:

(a) preparing at least one type of dendrimer-reagent complex, each said complex comprising a dendrimer covalently coupled to at least two different specific binding assay reagents, each said reagent having a defined analyte specificity, said specificity differing for each said reagent;

(b) adding effective amounts of each said type of said complex to a solid phase having interstices therein under conditions effecting immobilization of said complex on a delimited area of said solid phase, said solid phase retaining said interstices after adding said dendrimer-reagent complexes.

29. The method of claim 28, wherein each said type of said complex has specificity for a single analyte or a receptor of said single analyte.

30. The method of claim 28, wherein said reagents are selected from the group consisting of antibodies, antibody fragments, specific binding proteins and analytes.

31. The method of claim 28, wherein said covalently coupling of said reagent to said dendrimer is by C-S linkage carried out by combining SIAB-labeled moieties with sulfhydryl-containing moieties.

32. A solid phase composition for use in a specific binding assay, comprising:

(a) a solid phase having interstices therein; and (b) an analyte-binding component comprising at least one type of dendrimer-reagent complex, each said complex comprising a dendrimer covalently coupled to at least two different specific binding assay reagents, each said reagent having a defined analyte specificity, said specificity differing for each said reagent, each said complex being immobilized within a delimited area of said solid phase, said solid phase composition having interstices.

33. The solid phase composition of claim 32, wherein said reagents are selected from the group consisting of antibodies, antibody fragments, specific binding proteins and analytes.

34. The solid phase composition of claim 32, wherein each said type of said complex has specificity for a single analyte or receptor of said single analyte.

35. The solid phase composition of claim 32, wherein said solid phase comprises a mat of compressed fibers.

36. The solid phase composition of claim 35, wherein said solid phase is a glass fiber filter.

37. An article of manufacture comprising packaging material and at least two types of dendrimer-reagent complexes within said packaging material, each said dendrimer-reagent complex comprising a dendrimer covalently coupled to a specific binding assay reagent, said reagent having a defined analyte specificity, said specificity differing for each said type, wherein said packaging material contains a label or package insert that indicates said types of said complexes can be used in the method of claim 1 or 6.

38. An article of manufacture comprising packaging material and at least one type of dendrimer-reagent complex within said packaging material, said at least one complex comprising a dendrimer covalently coupled to at least two different specific binding assay reagents, each said reagent having a defined analyte specificity, said specificity differing for each said reagent, wherein said packaging material contains a label or package insert that indicates said at least one type of said complex can be used in the method of claim 19 or 23.

39. The method of claim 19, wherein each said type of said complex has specificity for at least two different analytes.

40. The method of claim 23, wherein each said type of said complex has specificity for at least two different analytes.

41. The method of claim 28, wherein each said type of said complex has specificity for at least two different analytes.

42. The solid phase composition of claim 32, wherein each said type of said complex has specificity for at least two different analytes.

43. The solid phase composition of claim 18, wherein said solid phase is a glass fiber filter.

* * * * *